(12) United States Patent
Wadstein

(10) Patent No.: US 7,557,094 B2
(45) Date of Patent: Jul. 7, 2009

(54) SKIN CREAM COMPOSITION

(75) Inventor: Jan Wadstein, Oslo (NO)

(73) Assignee: Ethics Cosmeceuticals AB (SE)

( * ) Notice: Subject to any disclaimer, the term of this patent is extended or adjusted under 35 U.S.C. 154(b) by 46 days.

(21) Appl. No.: 10/416,671

(22) PCT Filed: Nov. 1, 2001

(86) PCT No.: PCT/NO01/00437

§ 371 (c)(1),
(2), (4) Date: Sep. 22, 2003

(87) PCT Pub. No.: WO02/38123

PCT Pub. Date: May 16, 2002

(65) Prior Publication Data

US 2004/0043963 A1    Mar. 4, 2004

(30) Foreign Application Priority Data

Nov. 13, 2000   (NO) .................................. 20005718

(51) Int. Cl.
A61K 8/18 (2006.01)
A61K 8/02 (2006.01)
A61K 31/715 (2006.01)
A01N 43/04 (2006.01)

(52) U.S. Cl. ........................... 514/55; 514/58; 424/401; 424/59

(58) Field of Classification Search ..................... 514/55
See application file for complete search history.

(56) References Cited

U.S. PATENT DOCUMENTS 5,057,542 A * 10/1991 Leuba et al. .................. 514/55

FOREIGN PATENT DOCUMENTS

| DE | 19537297 A1 * | 1/1997 |
| EP | 0414608 A1 | 2/1991 |
| EP | 0637450 A2 | 2/1995 |
| WO | WO 9421225 A1 * | 9/1994 |
| WO | WO 9833476 A1 | 8/1998 |
| WO | WO 9926588 A2 * | 6/1999 |
| WO | WO 9932105 A1 | 7/1999 |
| WO | WO 9949840 A1 | 7/1999 |
| WO | WO 0037039 A1 | 6/2000 |
| WO | WO 0037040 A1 | 6/2000 |
| WO | WO 200059519 A2 * | 10/2000 |
| WO | WO 0108650 A1 | 2/2001 |

OTHER PUBLICATIONS

Remington (Remington: The Science and Practice of Pharmacy. 19th edition. pp. 1588-1589. (1995).*

* cited by examiner

*Primary Examiner*—Jake M. Vu
(74) *Attorney, Agent, or Firm*—Seyfarth Shaw LLP

(57) ABSTRACT

The present invention is related to compositions containing chitosan conjugated CLA (conjugated linoleic acid) and a chitosan conjugated Vitamin A or a β-cyclodextrin conjugated vitamin A. The invention also concerns the preparation of the compositions. The compositions according to the invention can be used as topical and cosmetic compositions as well as pharmaceutical compositions for treatment of atopical dermatitis, psoriasis eczema as well as eczema of different origins and solar dermatitis.

1 Claim, No Drawings

SKIN CREAM COMPOSITION

CROSS REFERENCE TO RELATED APPLICATION

This application claims the priority of Norwegian patent application Ser. No. 20005718, filed on Nov. 13, 2000.

FIELD OF THE INVENTION

The present invention relates to compositions, for application to (human and animal) skin and their use for improving the conditions and the appearance of skin. More particularly, it relates to novel skin creams, ointments, gels, salves, balms and solutions containing chitosan conjugated CLA (conjugated linoleic acid) and chitosan conjugated or β-cyclodextrin conjugated vitamin A for topical treatment of the skin structure. The invention also concerns the preparation of the compositions. The compositions according to the invention can be used for preparation of topical, cosmetic and pharmaceutical compositions. The prepared pharmaceutical compositions can be used for treatment of atopical dermatitis, psoriasis eczema as well as eczema of different origins and solar dermatitis. Furthermore, the compositions according to the invention can be used to improve the skin thickness and elasticity. The invention does also concern a method for improving skin thickness and skin elasticity.

BACKGROUND OF THE INVENTION

Skin creams of different kinds have been more and more popular and a lot of cosmetic companies are producing "miracle" creams. Scientists are quite aware of the necessity to "feed" the skin in different ways. Except from moistening factors, the skin needs also, as the whole body, nutrients as for instance vitamins, minerals, calories etc.

A number of new ointments or creams is introduced to the market each year, containing new agents believed to be good for the skin. However, it has been shown lately as reported in The Time (Aug. 28, 2000, pp. 34-38. *Facelift in a jar.*) that a number of these creams contains questionable ingredients and in amounts not meeting the amounts on the package leaflets.

The skin is the biggest organ of the human body and is very complex, due to its many functions. It should prevent the body from poisoning substances, which means it must have a strong barrier function. It should be able to sustain trauma of different kinds and if the skin is damaged it must be able to quickly repair itself. However, the skin is also sensitive to different factors such as, e.g., sun radiation which causes ageing of the skin. Many creams are on the market to protect against sunshine and others to reduce ageing of the skin, and a lot of research have been put into the fields of skin protection, skin reparation and anti-ageing.

Compounds that can feed the skin are fatty acids. Among them there is one recently discovered fatty acid called CLA (conjugated linoleic acid). The term CLA is a generic term used to reference both conjugated linoleic acid and conjugated linolenic acid. Since linoleic acid is an essential fatty acid, its conjugated forms are readily absorbed into lipids and fats. Theoretically, conversion of ordinary linoleic acid to conjugated linoleic acid results in eight isomers.

CLA is known to have several effects on different cell systems. In the body effects such as antioxidant effect, immune stimulant effect and antiallergenic effects are observed. Additionally CLA has been shown to promote cell generation in both animal and human subjects. It does also have effect on fat reduction and muscle building. For skin CLA could be an ideal substance to improve skin quality. However, due to its nature the major problem is to make it penetrate the skin and exert its effects directly in the skin.

Another nutrient is A-vitamin acid which has a well-documented effect on skin. In the cells A-vitamin acid has nutritional effects and promotes regeneration. However, this compound does also have side effects. Due to its irritant effect it can only be bought on prescription, and is used in certain skin diseases as acne, psoriasis, eczema and others. It is known that the fat-soluble vitamin A is harmless to the skin, and inert, but if it penetrates the skin cells it will immediately be hydrolysed to A-vitamin acid and can exert its beneficial effect without irritation. It has earlier been shown by Wadstein (1991) that vitamin A bound to a certain carrier (β-cyklodextrin) could penetrate the skin almost as effective as A-vitamin acid, but without the above mentioned side effects. Creams with this solution has successfully been sold for more than 10 years.

Bovien colostrum does also have a beneficial effect on the skin and can therefor be added to skin compositions. Colostrum concentrates normally contain IgG (gammaglobulin) which enhances fagocytosis; IgA which protects the mucosal surfaces; IgM which also enhance fagocytosis and is especially effective against micro-organisms; IgD which stimulates B-cells to produce antibodies and IgE which is associated with allergic reactions. Another important factor found in bovine colostrum is IGF-1 (growth factor) which is an important promoter of cell formation and promotes skin juvenation in skin compositions. The antibacterial effects of the immunoglobulins have a certain impact on the healing efficacy of the skin compositions, as it has been shown that bacterial infection occurs in 100% of eczema's and skin wounds.

Dryness of the skin is an other problem. Several substances (hydrogels) such as, for example, chitosan, carboxy methyl cellulose, cyclodextrins have been used to prevent this.

Chitosan is a deacetylated breakdown product of chitin which is one of the most abundant polymers in the nature after cellulose. Chitosan is prepared from chitin which for example may be produced from the waste in the shellfish industry where shrimps are processed. Chitin and chitosan both belong to the group of polysaccharides.

Chitosan has the properties of a gel and binds as such water and contributes to the moistening effect of the skin. As dryness of the skin is a major problem, the ability to bind water both treat and prevent this condition. Chitosan does also have an anti-microbial effect beginning at a concentration of about 0.4 wt % and upwards of the composition.

From the prior art several topical formulations for treatment of the skin comprising conjugated linoleic acid are known. WO-9932105 discloses a composition for topical use comprising CLA esters and a topical carrier. U.S. Pat. No. 6,019,990 discloses cosmetic formulations comprising a conjugated linoleic acid and an ester of conjugated linoleic acid. These formulations may also contain a UV absorbing compound. WO-0037040 describes a topical composition comprising (a) conjugated linoleic acid, and/or derivatives thereof comprising conjugated linoleic acid moieties, in which at least 50% by weight og the conjugated linoleic acid and/or moieties, is present as the cis 9 trans 11 and (b) a dermatologically acceptable carrier.

Also cosmetic preparations containing chitosan are known for example from U.S. Pat. No. 5,057,542 and Pittermann W. et al., *Efficiency of high molecular weight chitosan in skin care applications* in Chitin Handbook, R. A. A. Muzzarelli and M. G. Peter, eds., European Chitin Society, 1997.

Additionally cosmetic compositions containing both chitosan and linoleic acid are known form EP-A-414608, which discloses cosmetic compositions comprising chitosan, some glucosamine and at least one organic acid selected from gluconic acid and succinic acid. FR-2785179 describes cosmetic compositions containing a aqueous dispersion of particulate filmogenic polymers and a polyorganosiloxane polyester of the type dimethicone copolyol comprising ester groups derived from fatty acids of vegetable oils comprising mainly oleic acid. WO-9847487 discloses a drug delivery system containing a liquid crystalline phase and a reverse micellar liquid crystalline phase. U.S. Pat. No. 5,874,463 describes a hydroxy-kojic acid skin peel for treatment of hyperpigmentation, melasma, dyschromia, rhytides, photodamage and aging. And WO-9939700 discloses pharmaceutical compositions in form of nanoparticles comprising a composite material, consisting of at least one lipidic substance and of at least one amphiphilic substance and of a pharmaceutically active principle.

SUMMARY OF THE INVENTION

Contrary to the present invention none of the above publications are related to chitosan conjugated CLA compositions. The CLA skin compositions of the present invention are based on sophisticated research by combining scientific results from quite different areas, and the characteristic features of these skin compositions are the content of biological active components which can provide the skin with necessary nutrients.

The present invention has solved the problem of CLA's insufficient skin penetration by conjugating CLA with chitosan. In the chitosan conjugated CLA complex chitosan works as carrier that enables CLA to reach into the stratum corneum of the skin.

In a first aspect of the present invention there is provided a composition containing chitosan conjugated CLA (comjugated linoleic acid) and a chitosan conjugated Vitamin A or a β-cyclodextrin conjugated vitamin A, where the content of CLA is 0.1-99 wt %, the content of chitosan is 0.025-25 wt %, and the content of Vitamin A is 0.025-10 wt %.

Optionally the compositions can contain chitosan conjugated vitamin E as well as sun protective factor and/or bovien colostrum concentrate.

Optionally lactose can be included in certain compositions of the present invention for treatments where it is important to promote the growth of the natural occurring acidofilic bacteria's as in eczema's or wounded skin. Lactose is a carbohydrate that exhibit different effects such as promotion of absorption of calcium and other minerals and promotion of growth of acidofilic bacteria's.

Additionally the compositions of the present invention may contain ingredients and adjuvants commonly used in the art to prepare skin care compositions, for example anti-oxidants such as, e.g., tocopheryl acetate and tocopherol; conservation agents such as, e.g., methyl-p-hydroxybenzoate and acetyl-p-oxybenzoate; emulsifiers such as, e.g., Emulgator E 471 and E 472 c; fillers such as, e.g., olive oil, arachidis oleum, oleum soya, stearin, water; hydrogels such as triethanolamine, carboxy methyl cellulose, chitosan and resin.

Chitosan is also preferable due to its antibacterial effect which means that it is able to preserve the composition in addition to provide an antibacterial effect on the skin surface.

However, the unique property of chitosan to bind fat can also be used to bind other important nutrients such as A- and E-vitamins and to promote transport/increase penetration into the skin (See Pittermann W. et al., *Efficiency of high molecular weight chitosan in skin care applications* in Chitin Handbook, R. A. A. Muzzarelli and M. G. Peter, eds., European Chitin Society. 1997). The compositions of the present invention contain chitosan conjugated vitamin A or β-cyclodextrin conjugated A vitamin and optionally chitosan conjugated vitamin E. As mentioned above β-cyclodextrin, belonging to the polysaccharide group, can be used as a carrier but in our opinion chitosan is superior in this respect.

The chitosan conjugated vitamin E has two effects. Firstly, vitamin E, as an antioxidant, protects the oxidation of CLA and secondly, it has an antioxidant effect on the skin.

To regulate the pH of the compositions weak acids, normally used in compositions for application to the skin, can be used such as lactic acid. Lactic acid belongs to the AHA series of natural acids, but has less irritating effects than fruit acids. Also bicarbonate solutions such as sodium bicarbonate may be used to adjust the pH of the compositions. The pH of the compositions are adjusted to a pH between 2 and 8, preferably 5.5 which is an ideal acidity for active skincare.

As several of the ingredients are sensitive to sun radiation a sun screen may optionally be added. A sun protective factor of 1-30 is well suited, preferably a sun protective factor of 4 is used. The sun screen does give a protection both to the composition and the skin during the time when the composition is supposed to penetrate the skin surface.

In summary, these compositions are unique in the sense that they combine several active ingredients, which has previously not been possible.

DETAILED DESCRIPTION OF THE INVENTION

CLA (Conjugated Linoleic Acid)

The CLA isomers of most interest in the present invention are cis-9-trans-11-linoleic acid (c9t11) and trans-10-cis-12-linoleic acid (t10c12). These isomers are commonly known to give physiological benefits and are also easily prepared from natural sources. The CLA should preferably have 0.1-90% of each isomer, preferably in a 50:50 relation. Some suitable substances having the above mentioned characteristics are: CLA 80 (Tonalin), CLA isomer c9 t11 and CLA 80 isomer t10c12, which contain equal amounts of the two isomers, namely about 34,5% of each.

The amount of CLA in the composition in the form of chitosan conjugated CLA should be in the range of 0.1 wt % to 99 wt % of the composition, preferably 0.5 wt % to 70 wt % and most preferred 0.8 wt % to 40 wt %.

Chitosan

The degree of deacetylation is important for the properties of chitosan as is the molecular weight of the polymer. The percent of deacetylation in the chitosan used in the present compositions should be in the range of 70 to 95%, preferable 87-90%, while the preferred molecular weight of the chitosan used in this invention should be in the range of 5,000 to 50,000. The viscosity of the chitosan polymer itself should be in the range of 120-169 mPa·s, preferably about 140 mPa·s, determined in 1% acetic acid at 25° C., with a concentration of 1% chitosan (dry weight basis). One suitable substance having the above mentioned characteristics is Chitosan Biopolymer L112.

The amount of chitosan in the composition in the form of chitosan conjugated CLA and chitosan conjugated vitamin A should be in the range of 0.025 wt % to 25 wt % of the composition, preferably 0.1 wt % to 16 wt % and most preferred 0.5 wt % to 10 wt %.

Vitamin A

The compositions should contain vitamin A in an amount between 0.025 wt % to 10 wt %.

Bovien Colostrum

A bovien colostrum concentrate should preferably contain the following immunoglobulins in the given amounts:

| Immunoglobulin | Amount of total antibody content |
| --- | --- |
| IgG | 70-85% |
| IgA | about 15% |
| IgM | 5-10% |
| IgD | 0.2% |
| IgE | 0.002% |

Additionally the concentrate should contain IGF-1 in a concentration of about 250 ng/kg colostrum concentate.

One suitable colostrum consentrate comprising 60% pure immunoglobulins in the relative amounts described above is produced by Kemikalia AB, Lund, Sweden.

The amount of freeze-dried bovine colostrum powder (with the above content) included in the composition should be from 0.5 g up to 10 g per 100 g of the composition.

Chitosan Conjugated CLA

The ratio of CLA to chitosan in the chitosan conjugated CLA complex may be in the range of 25:1 to 1:2.

The preferred ratio of CLA (mixture with cis-9-trans-11-linoleic acid (c9t11) and trans-10-cis-12-linoleic acid (t10c12) in equivalent concentrations of the isomers) to chitosan in the chitosan conjugated CLA complex is about 4:1.

Chitosan Conjugated Vitamin A

The amount of chitosan conjugated vitamin A in the compositions should be in the range of 0.1 wt % to 50 wt % of the composition (i.e. about 2,000-45,000 IU). The ratio between chitosan and vitamin A in the chitosan conjugated vitamin A should be in the range of 1:25 to 1:1.

Preparation of Chitosan Conjugated CLA

To achieve a satisfactory conjugate the chitosan conjugated CLA should be prepared by heating CLA with chitosan at 70° C. with stirring for about half an hour. The complex formed is then allowed to slowly cooled to about 50° C.

Preparation of Chitosan Conjugated Vitamin A

To achieve a satisfactory conjugate the chitosan conjugated vitamin A should be prepared by heating A-vitamin palmitate together with chitosan at 55° C. with stirring for about half an hour. The complex is subsequently cooled to 50° C.

Preparation of Chitosan Conjugated Vitamin E

To achieve a satisfactory conjugate the chitosan conjugated vitamin E should be prepared by heating, e.g., E-vitamin palmitate together with chitosan at 55° C. with stirring for about half an hour. The complex is subsequently cooled to 50° C.

Preferred Embodiment

The preferred conjugation ratio of CLA (mixture with cis-9-trans-11-linoleic acid (c9t11) and trans-10-cis-12-linoleic acid (t10c12) in equivalent concentrations of the isomers) to chitosan is 4:1.

By conjugating the CLA with Chitosan (complex binding) this new conjugate is believed to be one ideally suited part of a new skin composition. Another is β-cyclodextrin conjugated vitamin A or chitosan conjugated vitamin A and together with bovine colostrum we have optimised the skin composition with regard to anti-ageing capacity, rejenuvating ability and moistening effect on the skin in deeper layers. Added should of course be vitamin E and sun protection factors which have 2 effects: 1) to protect the skin cream from oxidation and 2) protect the skin.

Additionally, the compositions also promotes the growth of natural skin acidophilus bacteria's and natural symbiotic skin flora.

The compositions according to the present invention can also be used for treatment of atopical dermatitis, psoriasis eczema as well as eczema of different origins and solar dermatitis.

The compositions according to the present invention can be used to prepare topical, cosmetic and pharmaceutical compositions depending on the adjuvants and other components added.

Furthermore, the compositions of the invention can be used to improve skin thickness and elasticity.

The invention also provides a method for improving the skin thickness and the skin elasticity. The method comprises application of a sufficient amount of a composition according to the invention on the skin of a human or animal subject.

The dosage will depend on the nature of the conditions being treated, and possible associated treatments. The daily dosage of the compositions will range from 0.5 to 10 g in one or more administrations.

The following examples illustrate the invention but do not limit it in any way.

Experimental Part

EXAMPLE 1

Preparation of CLA-Chitosan Skin Cream

The properties of the cream depends on CLA's join action with chitosan. To achieve a satisfactory conjugation between the active components the cream should be prepared as described below:

100 gram CLA 80 (Natural AS Oslo) is heated with 30 g Chitosan, Biopolymer L112 (Natural, Oslo) to 70° C. with stirring for about half an hour. The complex which is formed is then allowed to slowly cool to 50° C. 20 g A-vitamin palmitate (Roche) is heated to 55° C. together with 10 g Chitosan, Biopolymer L 112 (Natural,Oslo) with stirring for about half an hour. The complex is subsequently cooled to 50° C., and is then mixed into a cream base of standard type, heated to 50° C., together with the CLA-chitosan-complex of 50° C. in such a way that the total amount of CLA is 2 g, A-vitamin palmitate 0.2 g and the total amount of chitosan is 0.7 g.

The pH of the newly formed solution is adjusted with lactate or sodium bicarbonate to pH 5.0-5.5.

The additional ingredients are 1 wt % tocopheryl acetate and 0.2 wt % tocopherol as anti-oxidants.

In the final formulation sunscreen factor is added to obtain a sunscreen factor of approximately 4.

Traditional conservation agents such as for example methyl-p-hydroxybenzoat and/or acetyl-p-oxybenzoat are added during the final process in sufficient amounts.

The above formulation may be used for cosmetic purposes and to alleviate skin irritant conditions and solar dermatitis.

EXAMPLE 2

Gel Formulation 100 gram CLA 80 (Natural AS Oslo) is heated with 30 g Chitosan, Biopolymer L112 (Natural, Oslo) to 70° C. with stirring for about half an hour. The complex formed is then allowed to slowly cool to 50° C.

20 g A-vitamin palmitate (Roche) is heated to 55° C. together with 10 g Chitosan, Biopolymer L 112 (Natural,Oslo) with stirring for about half an hour. The complex is subsequently cooled to 50° C.

20 g tocopherol acetate is heated to 55° C. together with 10 g Chitosan, Biopolymer L 112 (Natural,Oslo) with stirring for about half an hour and 20 g tocopherol is heated to 55° C. together with 10 g Chitosan, Biopolymer L 112 (Natural, Oslo) with stirring for about half an hour. The complexes are subsequently cooled to 50° C., and are then mixed into Carbomer (carboxy methyl cellulose) heated to 50° C, together with the CLA-chitosan-complex of 50° C. Water is then added and pH of the newly formed solution is adjusted with lactate or sodium bicarbonate to pH 5.0-5.5. The final volume is adjusted to 100 ml with water. The amounts of the ingredients are: chitosan 0.5 wt %, tocopherol acetate 0.2 wt %, tocopherol 0.05 wt % and CLA 2 wt % and Carbomer 0.3 wt %.

In the final formulation sunscreen factor as well as traditional conservation agent may be added in sufficient amounts.

The above gel can be used to treat atopic dermatitis and psoriasis eczema as well as eczema of different origins and severe solar dermatitis.

EXAMPLE 3

Cream Formulation

| Formulation for day cream (100 ml) | |
|---|---|
| Ingredients | Amount |
| Arachidis oleum | 13 ml |
| Emulsifier, non-ionic | 6 g |
| Stearin | 6 g |
| CLA | 2 g |
| Chitosan | 0.5 g |
| Vit A densatum Ph. Eur. | 0.2 g |
| Methyl-p-hydroxybenzoate | 0.1 g |
| Acetyl-p-oxybenzoate | 0.1 g |
| Triethanolamine | 100 mg |
| Resin | 50 mg |
| Lactate until pH 4.5 | |
| Tocopherol | 100 mg |
| Distilled water | q.s. |
| Sun screen F6 (PABA) | 3% |

The formulation can be prepared in accordance with the above examples and is suitable for cosmetic use.

Example 4

Cream Formulation

| Formulation for nigth cream (100 ml) | |
|---|---|
| Ingredients | Amount |
| Arachidis oleum | 17.05 ml |
| Oleum soya | 19.5 ml |
| Emulgator E 471 and E 472 c | 6.2 g |
| CLA | 2 g |
| Chitosan | 0.5 g |
| Methyl-p-hydroxybenzoate | 0.143 g |
| Acetyl-p-oxybenzoate | 0.2 g |
| Vit A densatum Ph. Eur. | 0.2 |
| Tocopherol | 100 mg |
| Lactate until pH 4.5 | |
| Distilled water | q.s. |

The formulation can be prepared in accordance with the above examples and is suitable for cosmetic use.

EXAMPLE 5

Effect on Skin Thickness and Elasticity

The formulation prepared in example 1 containing chitosan conjugated CLA was tested in a pilot study.

Materials and Methods

The study was carried out as an open study in 20 healthy females aged between 40 and 60 years (mean 49.2 yrs) who applied the ointment on the right volar (protected part) of the right forearm. The left forearm was used as a control and was not treated. The total treatment period was 3 months and administration was bid (in the morning and in the evening) during the study period. The study was carried out in accordance with the revised Helsinki declaration. All subjects received information about the aim of the study before inclusion and participate voluntarily in the study.

Measurements of Skin Thickness and Skin Elasticity

The measurements of skin thickness and skin elasticity were performed by ultrasound using Dermascan and Dermaflex instruments, respectively (Cortex Inc., Aarhus, Denmark). Measurements were carried out at baseline, after 1 months and after 3 months, by the same person on all three occasions and measurements were performed at the mid-region of the volar part of the forearm. All measurements were in triplicate and average values used for statistical evaluation.

Self-Evaluation by the Participants

At the same time as the objective measurements were carried out, participants made a self-evaluation of skin quality using visual analogue scales of 10 cm with end-points of "no change" and "very pronounced change". Subjects were asked to score the global change in skin quality by placing a mark on the line between the endpoints. The distance from the endpoint (0 cm) to the mark was used as the score for the subject.

Statistical Methods

A significance level of 5% was used in the tests and two-tailed tests were applied. The one sample test was used analysing change over time within groups. Two-sample t-test were used to compare arms with regard to continues variables.

Results

The results from the skin thickness measurements are shown in Table 1. As can be seen from the table the ointment gave an increase in skin thickness of 51% as compared to no change for the untreated arm. This change is highly significant (p<0.01).

TABLE 1

Change in skin thickness (mm) after administration of the ointment and no treatment for 3 months in 20 females.

|  | Initially | After 1 month | After 3 months |
| --- | --- | --- | --- |
| Ointment Mean (SD) | 0.89 (0.13) | 1.10 (0.20) | 1.35 (0.19) |
| No treatment Mean (SD) | 0.90 (0.10) | 0.91 (0.11) | 0.89 (0.12) |

The viscoelastic properties of the skin is shown in table 2.

TABLE 2

Change in skin elasticity (%) after administration of the ointment for 3 months in 20 females

|  | Initially | After 1 month | After 3 months |
| --- | --- | --- | --- |
| Ointment Mean (SD) | 59.0 (8.0) | 70.0 (7.9) | 75.2 (8.5) |
| No treatment Mean (SD) | 61.0 (7.5) | 60.0 (8.0) | 61.5 (8.1) |

The results show that the elasticity is improved by 27% on the ointment treated arm while no change is observed on the control arm.

The self-evaluation shows impressing results. The average score was 7.9 cm. The participants felt that they got a smoother and more elastic skin. They also expressed that they were highly satisfied with the cosmetic properties of the ointment. The rapid penetration of the ointment into the skin was highly appreciated by the participants.

No tolerability problems were reported during the study. The tolerability was excellent. All participants would like to continue with the ointment.

The results from this study shows very good effects in improving skin thickness and elasticity. Compared to previous studies with β-cyclodextrin conjugated Vitamin A esters (Thom E., *Skin treatment with two different galenical formulations of retinyl palmitate in humans*. J Appl Cosmetology 1993, 11; 71-76; Thom E., Long-term effects after topical application of active retinyl palmitate. J Appl Cosmetology 1994,12; 45-50; and Thom E., *A comparative double-blind within subject study of the efficacy and tolerability of two different derivatives of Vitamin A on skin thickness and elasticity: retinoic acid and conjugated retinyl palmitate*. J Appl Cosmetology 1997,15; 133-138) the present results are better showing an average improvement in skin thickness and elasticity of 51% and 27%, respectively. The previous studies only showed an improvement of about 32% and 19%, respectively, using the same measuring devices. The average global score on the satisfaction of the present formulation is also impressive with an average final score of 7.9 cm.

The invention claimed is:

1. A process for the preparation of a composition consisting of a chitosan conjugated with conjugated linoleic acid and chitosan conjugated vitamin A, the process consisting of the steps of:
    heating a first batch of chitosan with conjugated linoleic acid at 70° C. for about 30 minutes to form a chitosan conjugated with conjugated linoleic acid;
    cooling the chitosan conjugated with conjugated linoleic acid to about 50°,
    heating a second batch of chitosan with vitamin A at 55° C. for about thirty minutes to form chitosan conjugated vitamin A complex; and
    mixing the chitosan conjugated vitamin A complex and the chitosan conjugated with conjugated linoleic acid at about 50° C.

* * * * *